United States Patent [19]

Wexler

[11] Patent Number: 4,576,958
[45] Date of Patent: Mar. 18, 1986

[54] ANTIHYPERTENSIVE 4,5-DIARYL-1H-IMIDAZOLE-2-METHANOL DERIVATIVES

[75] Inventor: Ruth R. Wexler, Wilmington, Del.

[73] Assignee: E. I. Du Pont de Nemours and Company, Wilmington, Del.

[21] Appl. No.: 573,214

[22] Filed: Jan. 23, 1984

[51] Int. Cl.[4] .................. C07D 233/54; A61K 31/415
[52] U.S. Cl. ..................................... 514/400; 548/342
[58] Field of Search .................... 548/342; 424/273 R; 514/400

[56] References Cited

U.S. PATENT DOCUMENTS 4,372,964  2/1983  Whitney .............................. 548/342

Primary Examiner—Henry R. Jiles
Assistant Examiner—Robert C. Whittenbaugh

[57] ABSTRACT

Antihypertensive 4-phenyl-5-(4-methylsulfonylphenyl)-α,α-bis(trifluoromethyl)-1H-imidazole-2-methanol derivatives are useful in the treatment of hypertension.

3 Claims, No Drawings

ANTIHYPERTENSIVE 4,5-DIARYL-1H-IMIDAZOLE-2-METHANOL DERIVATIVES

BACKGROUND OF THE INVENTION

1. Field of the Invention

This invention relates to imidazole methanol derivatives, pharmaceutical compositions containing them and methods of using them to treat hypertension.

2. Prior Information

U.S. Pat. No. 4,372,964, issued Feb. 3, 1983, to Joel G. Whitney describes antiinflammatory compounds of the formula

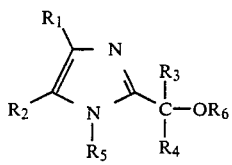

wherein $R_1$ and $R_2$ independently are 3-pyridyl, 2-thienyl or X—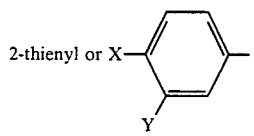—Y where X is H, F, Cl, Br, $C_1$-$C_2$ alkyl, $C_1$-$C_2$ alkoxy, di($C_1$-$C_2$ alkyl)amino or $CH_3S(O)_n$;
n=0, 1 or 2;
Y is H, F or Cl with the proviso that when Y is F or Cl, then X must be F or Cl;
$R_3$ and $R_4$ independently are H, $C_1$-$C_3$ alkyl, cyclopropyl, $CF_3$, $CF_2H$, $CF_2Cl$, $CF_3CF_2$ or $CF_3CF_2CF_2$;
with the proviso that no more than one of $R_3$ and $R_4$ can be H;
$R_5$=H or $C_1$-$C_3$ alkyl;
$R_6$=H, $C_1$-$C_3$ alkyl,

or —$COOR_7$;
where
$R_7$ is $C_1$-$C_2$ alkyl; with the proviso that
$R_5$ and $R_6$ cannot both be $C_1$-$C_3$ alkyl; a pharmaceutically suitable acid addition salt where $R_1$ or $R_2$ is 3-pyridyl or where X is dialkylamino, or a pharmaceutically suitable metal salt thereof when at least one of $R_5$ and $R_6$ is H.

Some compounds in U.S. Pat. No. 4,372,964 preferred for their antiinflammatory or analgesic properties are 4,5-bis-(4-fluoro or 4-methoxyphenyl)-α,α-bis(trifluoromethyl)-1H-imidazole-2-methanols.

SUMMARY OF THE INVENTION

According to the present invention there is provided a compound of the formula I

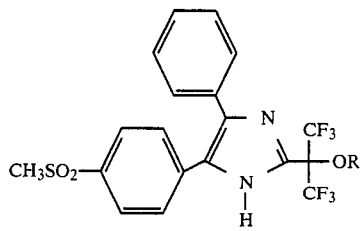

where R is H or $$-\overset{O}{\underset{\|}{C}}-CH_3,$$

or a pharmaceutically suitable salt thereof.

The compound 4-phenyl-5-(4-methylsulfonylphenyl)-α,α-bis(trifluoromethyl)-1H-imidazole-2-methanol is preferred.

Also provided are pharmaceutical compositions containing such compounds and methods of using them to treat hypertension.

The compounds of this invention fall within the general formula of U.S. Pat. No. 4,372,964, but have been found to be antihypertensive agents which lower blood pressure by vasodilatory action and which do not seem to have any significant side effects in rat studies.

SYNTHESIS

Compounds of Formula I can be prepared as follows: Friedel-Crafts acylation of thioanisole with phenylacetyl chloride results in the appropriate desoxybenzoin compound (II) which is then converted to the α-bromoketone utilizing bromine in a suitable solvent system such as methylene chloride and/or ether. The 4,5-diarylimidazole (III) is then prepared as described in Brederick, H, et al. *Chem. Ber.*, 86, 88 (1953), i.e., the α-halo-ketone is refluxed in formamide to give the requisite 4,5-diarylimidazole unsubstituted in the 2-position (III) (Scheme A).

Scheme A

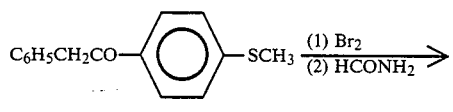

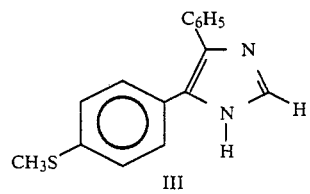

The compound of Formula V where R=H is best prepared by reacting the 4,5-diarylimidazole (III) with an appropriate protecting group reagent such as ethyl vinyl ether. The resulting 4,5-disubstituted-1-protected imidazole (IV) is then treated with a strong base such as n-butyl lithium (n-BuLi) in a suitable solvent such as tetrahydrofuran at low temperature followed by hexafluoroacetone (HFA), and then removal of the protecting group (Scheme B). The nature of the α-ethoxyethyl protecting group is such that it is stable to strong bases, but easily removed by acidic reagents. The synthesis of 4,5-diaryl-1H-imidazole-2-methanols is described in aforesaid U.S. Pat. No. 4,372,964 (column 4, line 60 to column 5, line 15).

Scheme B

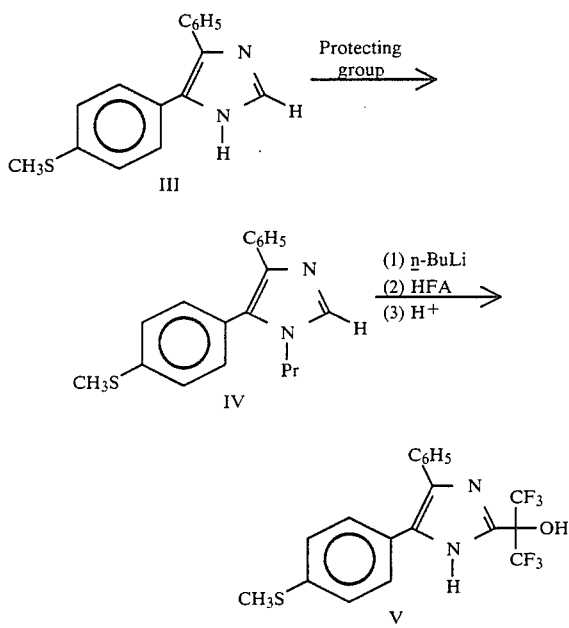

Oxidation of the methyl sulfide of Formula V to the sulfone (I) can be accomplished with potassium hydrogen persulfate (KHSO$_5$, commercially sold as Oxone ®) in a suitable solvent such as methanol (Scheme C) as described by B. M. Trost and D. P. Curran, *Tetrahedron Letters*, 22, 1287 (1981).

Scheme C

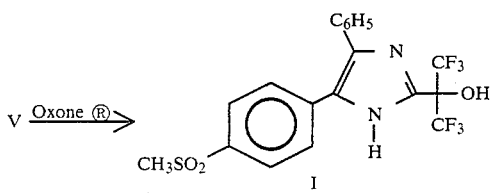

The compound of Formula I where R=C(O)CH$_3$ can be prepared from the compound of Formula I (R=H) by treatment with acetic anhydride in the presence of an acid such as p-toluenesulfonic acid at reflux in an inert solvent such as benzene, or toluene (Scheme D).

Scheme D

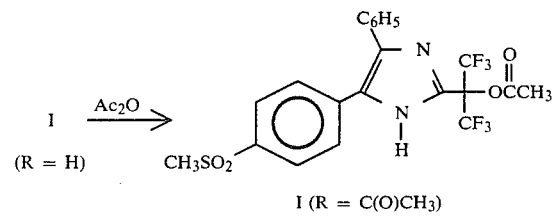

The preparation of these compounds is further illustrated by the following examples wherein all parts are by weight unless otherwise specified, and all temperatures are in degrees centigrade.

EXAMPLE 1

4-Phenyl-5-(4-methylsulfonylphenyl)-α,α-bis(trifluoromethyl)-1H-imidazole-2-methanol (I, R=H)

(A) 2-Phenyl-1-(4-methylthiophenyl)ethanone (II)

To a solution of 46.8 g (0.030 mole) of phenylacetyl chloride in dry methylene chloride (330 ml) was added 37.6 g (0.030 mole) of thioanisole. The solution was cooled to 5° in an ice-acetone bath, and anhydrous aluminum chloride (40.9 g, 0.031 mole) was added portionwise over 30 minutes at a rate to maintain the temperature constant at 5°. The reaction mixture was stirred at 5° for 3.5 hours, after which time the mixture was carefully poured into 1300 ml of aqueous 1N HCl and was stirred overnight. The layers were separated and the aqueous layer was extracted with methylene chloride (2×1l). The organic fractions were combined and washed with 1N hydrochloric acid (2×500 ml), 5% aqueous sodium hydroxide (2×500 ml) and brine (2×500 ml). The organic layer was dried over anhydrous magnesium sulfate and concentrated. The crystalline product was collected by filtration and washed with cold ethanol to afford 65.3 g (89%) of 2-phenyl-1-(4-methylthiophenyl)ethanone as a white solid, m.p. 98°–100°.

NMR (200 MHz, DMSO-d$_6$)δ2.50 (s, 3H), 4.30 (s, 2H), 7.17–7.47 (m, 7H) 7.93–8.0 (m, 2H).

(B) 2-Bromo-2-phenyl-1-(4-methylthiophenyl)ethanone

To a suspension of 30 g (0.12 mole) of 2-phenyl-1-(4-methylthiophenyl)ethanone in 45 ml of methylene chloride and 450 ml of ether was added dropwise a solution of 20.8 g (0.13 mole) of bromine in 65 ml of methylene chloride. The reaction mixture decolorized and became slightly exothermic. After stirring an additional 30 minutes, the reaction mixture was concentrated under vacuum. The crystalline product was collected by filtration and washed with hexane to give 36.3 g (91.5%) of 2-bromo-2-phenyl-1-(4-methylthiophenyl)ethanone as an off-white solid, m.p. 101°–103°.

NMR (200 MHz, CDCl$_3$)δ2.50 (s, 3H), 6.33 (s, 1H), 7.15–7.63 (m, 7H), 7.83–7.95 (m, 2H).

(C) 4-Phenyl-5-(4-methylthiophenyl)-1H-imidazole (III)

A mixture of 36 g of 2-bromo-2-phenyl-1-(4-methylthiophenyl)ethanone and 175 ml of formamide was refluxed under a dry air condenser for 2.5 hours. The reaction was cooled to 100° and 200 ml of water was added. The reaction was cooled to room temperature, and the product was filtered and washed with water and then ether. The solid was dried in a vacuum oven (75°) and then recrystallized from acetonitrile to afford 15.0 g (50%) of the title compound as a tan solid, m.p. 203°–206°. In a subsequent reaction the yield was improved to 65% by refluxing the reaction mixture for 3 hours.

NMR (200 MHz, DMSO-d$_6$)δ2.50 (s, 3H), 3.0–3.5 (bs, 1H), 7.13–7.63 (m, 9H), 7.8 (s, 1H).

(D)
4-Phenyl-5-(4-methylthiophenyl)-1-(α-ethoxyethyl)imidazole

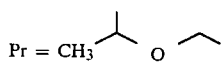

(IV)

A mixture of 12.0 g (0.045 mole) of 4-phenyl-5-(4-methylthiophenyl)-1H-imidazole, 6.7 g (0.052 mole) of dichloroacetic acid and 24.6 g (0.34 mole) of ethyl vinyl ether in 485 ml of toluene was heated at reflux for 3 hours. The reaction mixture was cooled to room temperature and was then stirred overnight with 130 ml of 25% aqueous sodium hydroxide. The organic layer was separated and the aqueous layer was extracted with ether (2X). The organic fractions were combined, washed with brine and dried over anhydrous potassium carbonate. Removal of the solvent under vacuum afforded 15.3 g of an oil. The product was used in the subsequent reaction without purification.

NMR (200 MHz, CDCl$_3$)δ1.0–1.2 (m, 3H), 1.63 (d, 3H), 2.47 (d, 3H), 3.13–3.50 (m, 2H), 5.0–5.18 (m, 1H), 7.05–7.50 (m, 9H), 7.88 (s, 1H).

(E)
4-Phenyl-5-(4-methylthiophenyl)-α,α-bis-(trifluoromethyl)-1H-imidazole-2-methanol (V)

To a stirred solution of 4-phenyl-5-(4-methylthiophenyl)-1-(α-ethoxyethyl)imidazole (15.5 g, 0.05 mole) in 175 ml of dry tetrahydrofuran was added 7.95 ml (0.052 mole) of N,N-tetramethylethylenediamine. The reaction mixture was cooled to −78° and 45.9 ml of 1.6 M n-butyl lithium in hexane was added dropwise. After stirring the mixture an additional 15 minutes, hexafluoroacetone (12.2 ml) was condensed in a jacketed addition funnel and added dropwise. The mixture was stirred for 1 hour with continued cooling and then 200 ml of saturated aqueous sodium bicarbonate solution was added dropwise. The reaction was warmed to room temperature, and the organic layer was separated. The solvent was evaporated in vacuo and the residue was stirred in 300 ml of ethanol and 300 ml of 2N aqueous hydrochloric acid. The ethanol was removed in vacuo and the reaction mixture was basified to pH=8 with saturated aqueous potassium carbonate. The product was extracted into ether, washed with 10% aqueous sodium bicarbonate and dried over anhydrous potassium carbonate. After concentration in vacuo, the residue was purified by flash chromatography on silica gel (85:15 hexane/ethyl acetate) followed by trituration with petroleum ether to afford 12.3 g of 4-phenyl-5-(4-methylthiophenyl)-α,α-bis(trifluoromethyl)-1H-imidazole-2-methanol, m.p. 119°–121°.

NMR (200 MHz, CDCl$_3$)δ2.50 (s, 3H), 5.88 (bs, 1H), 7.13–7.25 (m, 2H), 7.3–7.63 (m, 7H), 9.20 (bs, 1H).

Anal. Calcd for C$_{19}$H$_{14}$F$_6$N$_2$OS: C, 52.78; H, 3.24; N, 6.48; Found: C, 52.7, H, 3.5; N, 6.4.

(F)
4-Phenyl-5-(4-methylsulfonylphenyl)-α,α-bis(trifluoromethyl)-1H-imidazole-2-methanol (I, R=H)

A mixture of 4.0 g (9.25 mmoles) of 4-phenyl-5-(4-methylthiophenyl)-α,α-bis(trifluoromethyl)-1H-imidazole-2-methanol, 14.2 g (23.1 mmoles) of Oxone ® and 115 ml of methanol were stirred overnight. The inorganic solid was filtered off, and the filtrate was concentrated to dryness. The residue was partitioned between ethyl acetate and water and the organic layer was separated. The organic layer was washed with brine and water, dried over anhydrous magnesium sulfate and concentrated in vacuo. The product was recrystallized from a mixture of dichloroethane and butyl chloride affording 2.89 g (67%) of the title compound as a white solid, m.p. 223°–225°.

NMR (200 MHz, DMSO-d$_6$)δ3.20 (s, 3H), 7.25–7.52 (m, 5H), 7.60–8.0 (m, 4H), 9.18 (bs, 1H), 10.88 (bs, 1H).

Anal. Calcd for C$_{19}$H$_{14}$F$_6$N$_2$O$_3$S: C, 49.14; H, 3.02; N, 6.03; Found: C,49.2; H, 3.3; N 6.0.

EXAMPLE 2

4-Phenyl-5-(4-methyl sulfonylphenyl)-α,α-bis(trifluoromethyl imidazole-2-methanol, acetate ester To 2.5 g (5.39 mmole) of 4-phenyl-5-(4-methylsulfonylphenyl)-α,α-bis(trifluoromethyl)-1H-imidazole-2-methanol in 25 ml of toluene was added 0.90 ml of acetic anhydride followed by 0.25 g of p-toluenesulfonic acid. The reaction mixture was refluxed for approximately 48 hrs. The mixture was cooled to room temperature, poured into ethyl acetate, washed twice with brine, dried over anhydrous potassium carbonate and concentrated to dryness. The product was recrystallized from a mixture of butyl chloride and 1,2-dichloroethane to afford 1.23 g of the desired product as a white crystalline solid, mp 171°–173°.

Anal. Calcd for C$_{21}$H$_{16}$N$_2$F$_6$O$_4$S: C, 49.80; H, 3.16; N, 5.50; Found: C, 49.5; H, 3.4; N, 5.4.

The compounds of Examples 1 and 2 are summarized in Table 1.

TABLE 1

| Example No. | R | m.p. (°C.) |
|---|---|---|
| 1 | H | 223–225° |
| 2 | O<br>‖<br>CCH$_3$ | 171–173° |

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.05 to 10 milligrams per kilogram of body weight. Ordinarily, from 0.1 to 10, and preferably 0.2 to 5, milligams per kilogram per day in one or more applications per day is effective to obtain desired results.

The antihypertensive activity of the compounds of this invention was evidenced by tests conducted in spontaneously hypertensive rats (SHR). Graded dose levels of each compound were administered orally to groups of 8 such hypertensive rats. The compound was prepared in an aqueous 0.25% methylcellulose vehicle and administered at a volume to body weight ratio of 5.0 ml/kg. A group of hypertensive rats receiving the aqueous vehicle by the same route served as controls for each test. At various intervals of time after treatment, usually 90 minutes, the systolic arterial blood pressure of each rat was determined by modification of the microphone-manometer technique [Friedman, M. and Freed, S. C., *Proc. Soc. Exp. Biol. and Med.*, 70, 670 (1949)]. That dose of compound which produced a 30 mm mercury (mm Hg) reduction in blood pressure when compared to the mean systolic arterial blood pressure of the control animals was then determined (Effective Dose 30). For example, an ED30 of 0.76 mg/kg orally was obtained with the compound of Example 1 and an ED30 of 0.72 mg/kg was obtained with the compound of Example 2.

The hypotensive activity of the compound of Example 1 was also demonstrated by tests in normotensive unanesthetized dogs. This test in unanesthetized dogs was conducted to determine oral potency and duration of action.

Mongrel dogs of both sexes (5.4–14.0 kg) had polyethylene cannulas implanted in the femoral artery and vein under thiopental sodium anesthesia (20 mg/kg i.v.). The cannulas were passed subcutaneously, exteriorized through a small incision in the patellar region, and the leg bandaged. On the following morning, the fasted animals were placed in canvas slings. Blood pressure was recorded through the femoral artery cannula attached to a Statham pressure transducer; heart rate was recorded from Lead II of the electrocardiogram using subdermal needle electrodes and both blood pressure and heart rate were recorded continuously on a Grass polygraph. After a 30 minute stabilization period, groups of 6-8 dogs were given the compound of Example 1 at either 2.25, 4.5, 9 or 18 mg/kg orally at a volume to body ratio of 2 ml/kg. The compound was suspended in 0.25% Methocel ® with glycerin added as a wetting agent to a concentration of 3%. Blood pressure and heart rate were followed for an additional 6 hours.

Electrocardiographic time intervals were measured from Lead II at 0, 60, 120 and 360 minutes post dose. The ED30 (dose required to reduce mean arterial blood pressure by 30 mm Hg) for blood pressure lowering was calculated by linear regression using the maximum mean blood pressure decrease at each dose level. Statistical analyses were performed using a one factor analysis of variance with repeated measurements and Duncan's multiple range test.

The compound of Example 1 produced a dose-related reduction in arterial blood pressure which reached a peak within 80 minutes after dosing and which was maintained for at least 6 hours at 4.5, 9, and 18 mg/kg. A log dose-response regression line showed an oral ED30 of 16.5 mg/kg. Heart rate was significantly increased at each dose level within 20 minutes after dosing and remained elevated for 6 hours. This increase in heart rate did not grade with dose.

Analysis of the electrocardiogram revealed no significant changes in PR, QRS, or $QT_c$ time interval durations nor ventricular arrhythmias. Thus, no adverse cardiographic changes were observed.

What is claimed is:

1. A method of treating hypertension in a mammal comprising administering to the mammal an antihypertensive amount of a compound of the formula

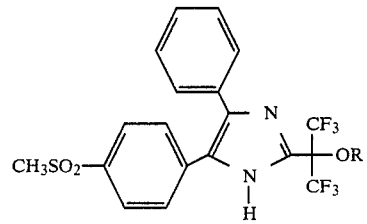

where R is H or

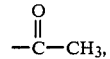

or a pharmaceutically suitable salt thereof.

2. The method of claim 1 wherein the compound is 4-phenyl-5-(4-methylsulfonylphenyl)-α,α-bis(trifluoromethyl)-1H-imidazole-2-methanol.

3. The method of claim 1 wherein the compound is 4-phenyl-5-(4-methylsulfonylphenyl)-α,α-bis(trifluoromethyl)-1H-imidazole-2-methanol, acetate ester.

* * * * *